United States Patent
Foroozan et al.

(10) Patent No.: US 12,042,256 B2
(45) Date of Patent: Jul. 23, 2024

(54) SYSTEMS AND METHODS FOR POWER REDUCTION FOR WEARABLE BIOMETRIC MONITORING DEVICES USING SIGNAL QUALITY METRICS

(71) Applicant: Analog Devices International Unlimited Company, Limerick (IE)

(72) Inventors: Foroohar Foroozan, Richmond Hill (CA); Di Xue, Toronto (CA); Wei Ken Fang, Richmond Hill (CA); Giuseppe Scelsi, Lower Templestowe (AU); Yih Yi Wu, Toronto (CA)

(73) Assignee: Analog Devices International Unlimited Company, Limerick (IE)

( * ) Notice: Subject to any disclaimer, the term of this patent is extended or adjusted under 35 U.S.C. 154(b) by 1004 days.

(21) Appl. No.: 16/853,395

(22) Filed: Apr. 20, 2020

(65) Prior Publication Data
US 2020/0337574 A1    Oct. 29, 2020

Related U.S. Application Data

(60) Provisional application No. 62/838,139, filed on Apr. 24, 2019.

(51) Int. Cl.
*A61B 5/024* (2006.01)
*A61B 5/00* (2006.01)
*A61B 5/0225* (2006.01)

(52) U.S. Cl.
CPC ...... *A61B 5/02427* (2013.01); *A61B 5/02255* (2013.01); *A61B 5/02438* (2013.01); *A61B 5/7203* (2013.01); *A61B 5/7207* (2013.01); *A61B 5/7221* (2013.01); *A61B 5/7264* (2013.01); *A61B 2560/0209* (2013.01)

(58) Field of Classification Search
None
See application file for complete search history.

(56) References Cited

U.S. PATENT DOCUMENTS

| | | | | |
|---|---|---|---|---|
| 8,478,389 B1* | 7/2013 | Brockway | ............ | G16H 50/30 |
| | | | | 600/509 |
| 2009/0299675 A1* | 12/2009 | Isaacson | ............ | A61B 5/14551 |
| | | | | 702/104 |
| 2011/0066051 A1* | 3/2011 | Moon | ................ | A61B 5/02225 |
| | | | | 600/509 |
| 2012/0310060 A1* | 12/2012 | Baker, Jr. | ........... | A61B 5/14551 |
| | | | | 600/324 |

OTHER PUBLICATIONS

McLeod et al., *A Smarter Way to Find Pitch*, Jan. 2005, 4 pages.
(Continued)

*Primary Examiner* — Michael R Bloch
(74) *Attorney, Agent, or Firm* — ARENTFOX SCHIFF LLP

(57) ABSTRACT

One embodiment is a method comprising collecting photoplethysmography ("PPG") data associated with a user using a biometric monitoring device; extracting a signal quality metric ("SQM") from the collected PPG data; classifying the PPG data signal based on the extracted SQM into one of a plurality of signal quality levels; and determining based on the classification whether to increase, decrease, or maintain a power level of an LED of the biometric monitoring device.

20 Claims, 12 Drawing Sheets

(56) References Cited

OTHER PUBLICATIONS

Atef et al., *A Fully Integrated High-Sensitivity Wide Dynamic Range PPG Sensor with an Integrated Photodiode and an Automatic Dimming Control LED Driver*, IEEE Sensors Journal, vol. 18, No. 2, Jan. 15, 2018, 8 pages.

Allen et al., *Assessing ECG Signal Quality on a Coronary Care Unit*, Physiological Measurement, 1996, 11 pages.

Li et al., *Dynamic Time Warping and Machine Learning for Signal Quality Assessment of Pulsatile Signals*, 13 pages.

Pelaez et al., *LED Power Reduction Trade-Offs for Ambulatory Pulse Oximetry*, Proceedings of the $29^{th}$ Annual International Conference of the IEEE EMBS Cite Internationale, Lyon, France, Aug. 23-26, 2007, 4 pages.

Kim et al., *Low-Power Photoplethysmogram Acquisition Integrated Circuits with Robust Light Interference Compensation*, MDPI, Sensors 2016, 11 pages.

Li et al., *Onboard Tagging for Real-Time Quality Assessment of Photoplethysmograms Acquired by a Wireless Reflectance Pulse Oximeter*, IEEE Transactions on Biomedical Circuits and Systems, vol. 6, No. 1, Feb. 2012, 10 pages.

Elgendi, *Optimal Signal Quality Index for Photoplethysmogram Signals*, MDPI, Bioengineering 2016, 15 pages.

Gawali et al., *Recent Trends in Energy Management of Wireless Wearable Bio Sensor Design*, 2017 $11^{th}$ International Conference on Intelligent Systems and Control (ISCO), © 2017 IEEE, 5 pages.

Li et al., *Robust Heart Rate Estimation from Multiple Asynchronous Noisy Sources Using Signal Quality Indices and a Kalman Filter*, National Institute of Health, Jan. 2008, 22 pages.

Orphanidou et al., *Signal-Quality Indicies for the Electrocardiogram and Photoplethysmogram: Derivation and Applications to Wireless Monitoring*, IEEE Journal of Biomedical and Health Informatics, vol. 19, No. 3, May 2015, 7 pages.

Chen et al., *System-Level Design Trade-offs for Truly Wearable Wireless Medical Devices*, $32^{nd}$ Annual International Conference of the IEEE EMBS, Buenos Aires, Argentina, Aug. 31-Sep. 4, 2010, 4 pages.

Ghasemzadeh et al., *Ultra Low-Power Signal Processing in Wearable Monitoring Systems: A Tiered Screening Architecture with Optimal Bit Resolution*, ACM Transactions on Embedded Computing Systems, vol. 13, No. 1, Article 9, Aug. 2013, 23 pages.

Cvetkovic et al., *Wavelet Transform Feature Extraction from Human PPG, ECG, and EEG Signal Responses to ELM PEMF Exposures: A Pilot Study*, Elsevier, 2007, 14 pages.

* cited by examiner

SYSTEMS AND METHODS FOR POWER REDUCTION FOR WEARABLE BIOMETRIC MONITORING DEVICES USING SIGNAL QUALITY METRICS

CROSS-REFERENCE TO RELATED APPLICATION

This patent application claims the benefit of the filing date of U.S. Provisional Patent Application Ser. No. 62/838,139, filed on Apr. 24, 2019, and entitled "SYSTEMS AND METHODS FOR POWER REDUCTION FOR WEARABLE BIOMETRIC MONITORING DEVICES USING SIGNAL QUALITY METRICS," the content of which is hereby expressly incorporated by reference.

FIELD OF THE DISCLOSURE

This disclosure relates generally to the field of wearable monitoring devices and, more particularly, to systems and methods for power optimization for such devices using signal quality metrics ("SQMs").

BACKGROUND

Modern electronics are ubiquitous in healthcare. For example, monitoring devices often include electronic components and algorithms to sense, measure, and monitor users. Monitoring equipment can measure vital signs such as respiration rate, oxygen level in the blood, heart rate, and so on. Not only are monitoring devices used in the clinical setting, monitoring devices are also used often in sports equipment and consumer electronics.

One important measurement performed by many of the monitoring devices is heart rate, typically measured in beats per minute (BPM). Many solutions for measuring heart rate are available on the market today. For instance, electronic heart rate monitors can be found in the form of battery-operated chest straps and watches and include sensors for generating photoplethysmography (PPG) data used in tracking a user's heart rate, for example.

Maximizing battery life without compromising signal quality is a key requirement in optimizing the design of a wearable monitoring device system. The light emitting diode ("LED") power consumption represents the highest power consumption in a PPG system. Conventional methods for calibration of LED settings focus only on DC level of the PPG signals and the power setting is selected quickly within one second of the initial data. Such methods are based on assuming a noise model for the Analog Front-End ("AFE") for the optical sensors, which noise model may be derived from reflector type of testing in a lab.

SUMMARY

One embodiment is a method comprising collecting photoplethysmography ("PPG") data associated with a user using a wearable monitoring device; extracting a signal quality metric ("SQM") from the collected PPG data; classifying the PPG data based on the extracted SQM into one of a plurality of signal quality levels; and determining based on the classification whether to increase, decrease, or maintain a power level of an LED of the wearable monitoring device.

Another embodiment is a system comprising an optical sensor for producing photoplethysmography ("PPG") data associated with a user; and a processor module configured for extracting a signal quality metric ("SQM") from the collected PPG data; classifying the PPG data based on the extracted SQM into one of a plurality of signal quality levels; and determining based on the classification whether to increase, decrease, or maintain a power level of an LED of the wearable monitoring device.

Yet another embodiment is a method comprising generating a photoplethysmography ("PPG") signal associated with a user using a wearable monitoring device comprising an optical sensor and a processing module; evaluating a quality of the PPG signal; classifying the PPG signal into one of a plurality of signal quality levels based on the evaluated quality; determining based on the classification whether to increase, decrease, or maintain a power level of an LED of the optical sensor; and adjusting a power level of the LED based on results of the determining.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

Maximizing battery life without compromising signal quality is a key requirement in optimizing the design of a wearable monitoring device system. The light emitting diode ("LED") power consumption represents the highest power consumption in a photoplethysmogram ("PPG"). Conventional methods for calibration of LED settings focus only on DC level of the PPG signals and the power setting is selected quickly within one second of the initial data. Such methods are based on assuming a noise model for the Analog Front-End ("AFE") for the optical sensors, which noise model may be derived from reflector type of testing in a lab.

In accordance with features of embodiments described herein, an LED power optimization system includes an Automatic Gain Control (AGC) embedded algorithm for photoplethysmographic (PPG) sensors that runs in real time and uses a number of statistical and spectral characteristics of raw and filtered PPG signals, referred to as a multi-dimensional SQMs, from PPG signals measured on a body part of a subject (or user) using a wearable monitoring device, for example.

PPG sensors are widely deployed in wearable health monitoring devices, such as cardiovascular monitoring devices and vital signs monitoring (VSM) devices. PPG sensors may be used as the source of arterial oxygen saturation (SaO2) and heart rate (HR) signals and may also serve as a simple and low cost technique for blood volume change detection in a microvascular bed of tissue, blood pressure and cardiac output estimation, respiration rate estimation, and vascular assessment. A PPG signal is composed of AC and DC components. The AC component is related to the blood pulsatile in the artery synchronized with the heartbeat, whereas the DC component is related to the venous blood volume and the non-pulsatile component in the artery.

Figure 1:
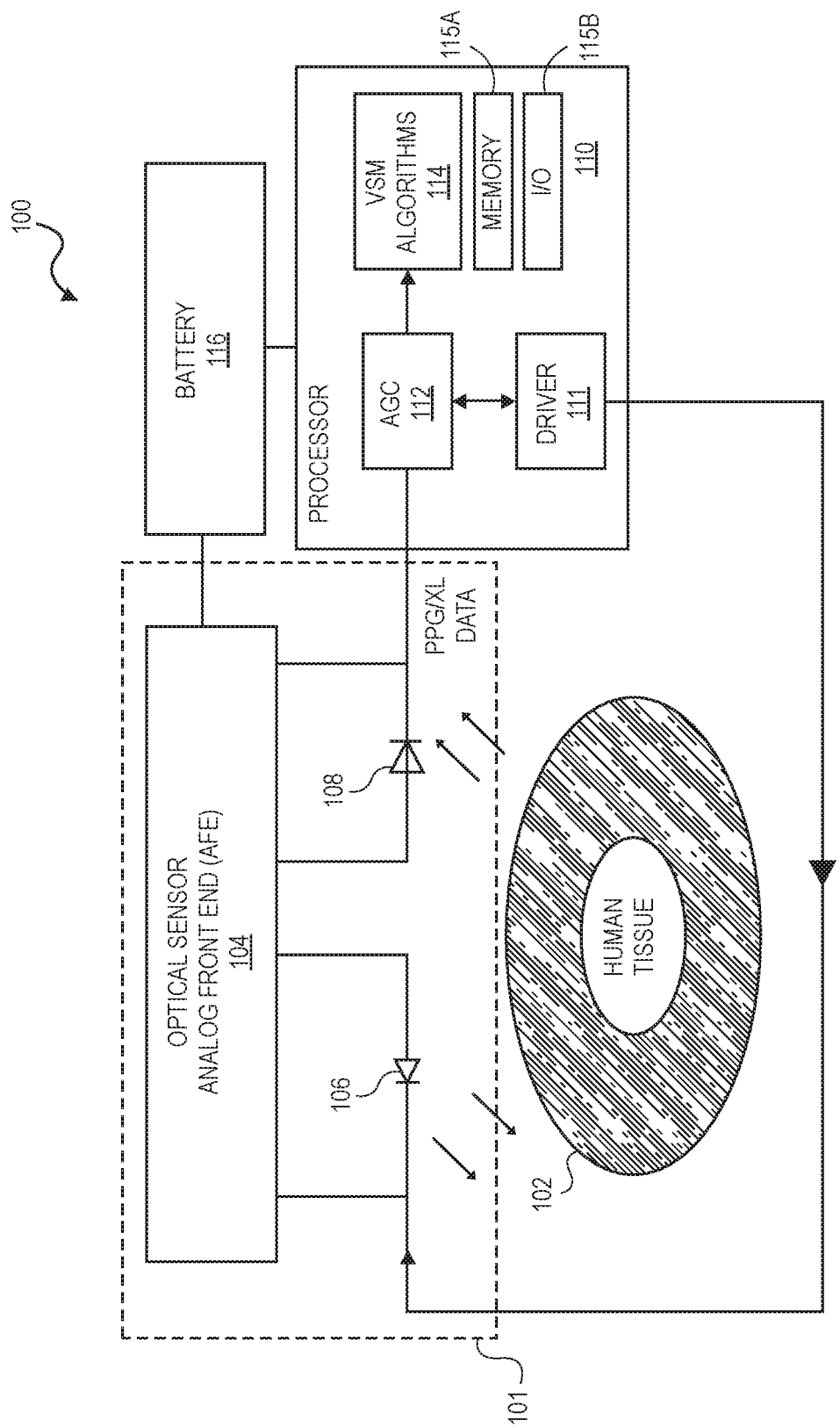
FIG. 1 is a block diagram of a system for implementing techniques for power reduction for wearable monitoring device using SQMs in accordance with embodiments described herein.

Referring now to FIG. 1, illustrated therein is a block diagram of a multi-sensory monitoring system 100 in accordance with embodiments described herein for measuring multiple vital signs of a user. In particular, FIG. 1 illustrates the monitoring system's spatial relationship with a portion of the user. In an example embodiment in which the system 100 is used to monitor the user's heart rate, for example, a method of PPG is used in which the user's HR maybe measured passively or indirectly based on changes in light absorption in the skin as blood is pushed through the arteries. Changes in blood volume as blood is pumped through the arteries results in a variation in the amount of received light, which is translated into electrical pulses by an optical sensor. The pulses in the signal can then be used in extracting a heart rate.

It will be recognized that multi-sensory monitoring systems described herein are not limited to the particular example shown in FIG. 1. Although the disclosure does not describe other types of monitors in detail, one skilled in the art would appreciate that these challenges are also applicable in other types of multi-sensory monitors or other types of devices providing multi-sensory monitoring functions, or even devices utilizing other types of sensing mechanisms.

Referring again to FIG. 1, the system 100 includes a wearable monitoring device comprising an optical sensing system 101 disposed in proximity to the skin of a body part 102 of the user. The optical sensing system 101 includes an analog front end 104 comprising circuitry for supporting operations of a light source 106 and an optical sensor 108. The light source 106 can emit light within a range of wavelengths suitable for the application. In some embodiments, the light source 106 and the optical sensor 108 can be provided separately, or a light source can be biased to function as an optical sensor. For instance, a red LED can be used as a red light source and a red optical detector. In some embodiments, both the light source 106 and optical sensor 108 can be provided proximate one another in a housing or member of the system 100 or in any suitable configuration where the optical sensor 108 can measure absorption of light (as generated by the light source 106) by the part 102 of the user. In operation, the light source 106 shines a light onto a part 102 of the user and the optical sensor 108 measures light incident onto the optical sensor, which can include light being reflected from the part 102 as well as ambient light. Various parts of the user can be used as body part 102, e.g., a finger, an arm, a forehead, an ear, chest, a leg, a toe, etc., as long as changes in the volume of blood can be measured relatively easily. The part 102 can in some cases be internal to the body of the user.

Generally speaking, if the monitoring device can be affixed to the body part 102 of the user securely and maintain relatively stable contact with the body part during use, the input signal provided by the optical sensor would exhibit very little noise. However, in many scenarios, the monitoring device is not particularly securely attached to the body part 102 (even with the use of a band, a strap, adhesive, or other suitable attachments). In other scenarios, it may be neither desirable nor comfortable for the user to have the monitoring device securely adhered or attached to the body part 102. In such scenarios, the signal provided by the optical sensor will be affected by noise from ambient light, artifacts caused by motion of the heart rate monitoring apparatus, or by some other noise source. As a result, correctly analyzing the signal (e.g., to detect the user's heart rate) in these non-ideal scenarios can be challenging and can result in irregular or erroneous results.

To address this issue, the system 100 may further include a mechanism that discards certain portions of data if the data is deemed unusable. Such a mechanism may include an accelerometer 109 for generating accelerometer (XL) signals indicative of the motion of the system 100.

Analog front end 104 may drive the light source 106 and receives signals from optical sensor 108, accelerometer 109, and any other sensors. In some embodiments, the analog front end 104 can convert (if desired) analog input signals to data samples of the analog input signal. The analog front end can communicate with a processor 110 to provide the data samples (e.g., XL and PPG) for processing.

In various embodiments, the processor 110 can include several special application specific parts or modules, electronic circuits, and/or programmable logic gates specially arranged for processing the data samples of the input signal to track the slow varying frequency. The processor 110 can be a digital signal processor provided with application specific components to perform power reduction functions described herein and/or the processor can execute special instructions (stored on non-transitory computer readable-medium) for carrying out various methods of power reduction as described herein.

In certain embodiments, the processor processes signals received from the optical sensing system 101 and for provides control and other signals to the system 101 via a driver 111. In certain embodiments, processor module 110 includes hardware and software necessary for executing AGC algorithms 112 and VSM algorithms 114 in connection with the signals received from and provided to the sensor 108 for purposes to be described in detail below. Processor may further include memory and storage 115A and input/output (I/O) and other communications devices 115B as necessary for performing functions of embodiments described herein. Power is provided to components of system 100 via a battery 116.

In some embodiments, system 100 may be implemented as a watch, wherein the body part 102 corresponds to the user's wrist. The system 100 may integrate PPG, electrocardiogram (ECG), bio-electric impedance, motion (e.g., accelerometer), and surface temperature measurements in a small battery-operated system that uses a combination of sensors (represented in FIG. 1 by optical sensor 108), embedded processors, and wireless communications to send data to a remote smart device. In accordance with features of embodiments described herein, an interface is provided between a processor and sensor subsystems of the system and peripherals that interact with the system.

It will be recognized that maximizing battery life without compromising signal quality is a key requirement in optimizing the design of wearable monitoring systems, such as the. LED power consumption represents the highest percentage of overall power consumption in optical sensors. Various research efforts have focused on optimization of the power of wearable, wireless devices at the system level, at the algorithm level, and at the circuit level. At the circuit level, optimizing power by LED duty cycle reduction and light power minimization has been previously proposed. An automatic dimming control has been implemented in some previous systems to reduce the LED current, and therefore the power consumed thereby. Because the AC part of PPG signals is important for all of the VSM algorithms, the signal quality of the PPG should not be compromised by power optimization techniques employed. Accordingly, power optimization algorithms based on the individual wearing the platform are essential in these systems. An AGC algorithm in accordance with embodiments described herein measures PPG signal quality and changes the LED settings (sampling frequency, LED current, and/or the number of pulses) on the fly to save power and/or optimize power consumption. A number of statistical and spectral characteristics of raw and filtered PPG signals, referred to as multi-dimensional SQMs, from the measured PPG signals on subjects' skin are evaluated. While SQM has been previously proposed for anomaly detection for PPG and electrocardiogram (ECG) signals, embodiments herein use PPG SQMs for power optimization and propose a new clarity metric as the main PPG SQM. Additionally, in accordance with features of embodiments described herein, the power optimization functionality is lightweight enough to be executed in an embedded processor (e.g., an ARM Cortex M3) in real time.

Figure 2:
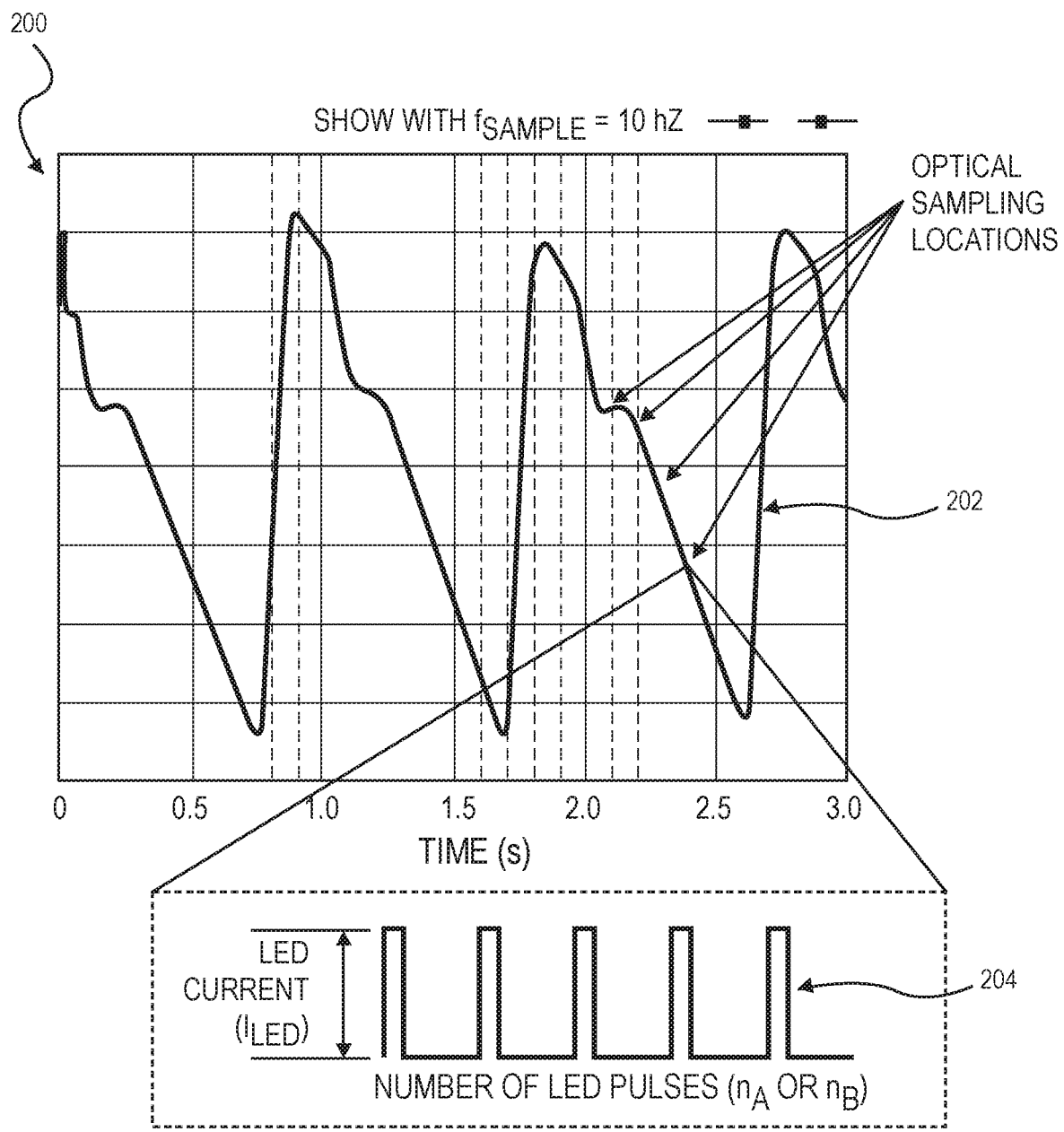
FIG. 2 illustrates LED settings for PPG signals in a system for power reduction for wearable monitoring device using SQMs in accordance with embodiments described herein.

FIG. 2 is a graph 200 illustrating a relationship between LED parameter settings 202 (e.g., LED current and number of pulses) and a quality of a resulting PPG signal 204. For example, increasing LED current and/or number of LED pulses per sample will result in a higher quality PPG signal but will result in consumption of a greater amount of power (a concern for a battery-powered device). On the other hand, decreasing LED current and/or number of LED pulses per sample will result in less power being consumed by the optical sensor, but will also result in a lower quality PPG signal. Pulse width, pulse period, and number of pulses per sample are parameters that are programmed into the monitoring device.

Figure 3:
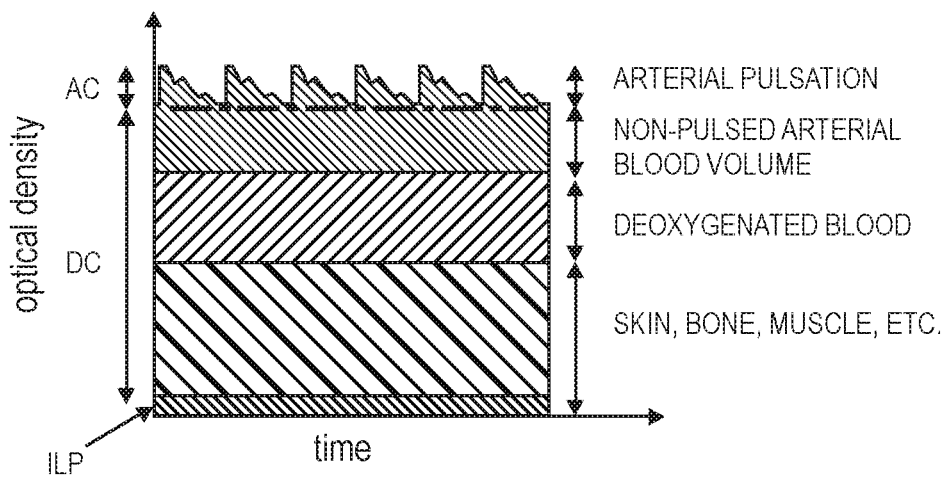
FIG. 3 illustrates a sample PPG signal, including alternating current (AC) and direct current (DC) components, detected by a wearable biometric monitoring device in accordance with embodiments described herein.

FIG. 3 is a graph illustrating various DC and AC components of an example PPG signal in terms of optical density over time.

PPG sensors are widely deployed in wearable health monitoring devices, such as cardiovascular monitoring devices and vital signs monitoring (VSM) devices. PPG sensors may be used as the source of arterial oxygen saturation (SaO2) and heart rate (HR) signals and may also serve as a simple and low cost technique for blood volume change detection in a microvascular bed of tissue, blood pressure and cardiac output estimation, respiration rate estimation, and vascular assessment. A PPG signal is composed of AC and DC components. The AC component is related to the blood pulsatile in the artery synchronized with the heartbeat, whereas the DC component is related to the venous blood volume and the non-pulsatile component in the artery.

Figure 4:
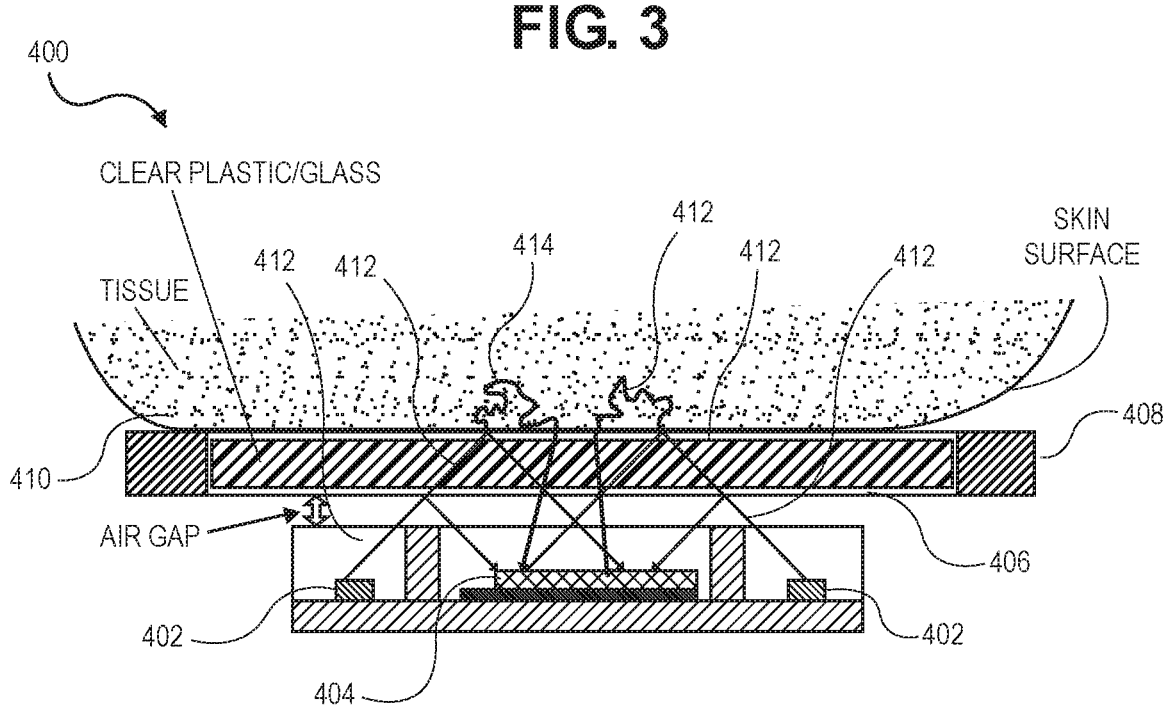
FIG. 4 illustrates the concept of internal light pollution due to the reflections of photons from the glass of a wearable monitoring device or from human skin.

Important PPG signal parameters include modulation index (MI), signal-to-noise ratio (SNR), and Current Transfer Ratio (CTR). The MI is the ratio of the AC components of a PPG signal to the DC components of the PPG signal. The MI depends on system parameters and on characteristics of the individual wearing the optical sensor and may range from as low as 0.1% or less to as high as 3%. The MI is related to the Perfusion Index (PI), which is the ratio of pulsatile blood flow to non-pulsatile, or static, blood in the peripheral tissue. Referring now to FIG. 4, illustrated therein is the concept of internal light pollution (ILP) in a wearable biometric monitoring device system 400, which is the amount of light from an LED 402 that is reflected back to a photodiode 404 (e.g., due to reflections of photons from a glass or plastic surface 406 of a wearable device 408 of the system 400 or from a surface 410 of the skin of a subject) that contains no useful information and merely consumes dynamic range and limits the attainable SNR level of the system 400. The PPG signal is maximized when LED light penetrates the skin surface, enters the blood, and scatters back to the sensor.

Lines 412 represent the PPG signal, whereas lines 414 represent a DC offset. This is where the difference between MI and PI lies; the MI contains the ILP on top of other DC components of the PPG signals. Additionally, the MI is dependent on the LED-to-photodiode spacing, the subject physiology, the ILP, and the monitoring site (e.g., wrist, finger, etc.), but independent of the LED current, photodiode size, the subject skin color, and the AFE gain. The CTR, on the other hand, is the amount of photodiode signal given a certain amount of the LED current ($I_{LED}$) and is expressed in nA/mA. CTR of an optical system is measured for a specific use case and is dependent on the LED-to-photodiode spacing, ILP, skin color (include tattoos, hair, etc.) photodiode area, and the LED efficiency. CTR is independent of the amount of LED light (because the DC portion of the signal ($S_{DC}$) will track proportionally) and AFE gain. In summary:

$$CTR(\text{nA/mA})=S_{DC}(\text{nA})/I_{LED}(\text{mA})$$

For initial LED calibration, the worst-case scenario of lowest MI and highest SNR is assumed. At this stage, the skin tone is evaluated based on the CTR. The calculations are based on a static noise model of the AFE and the DC level of the signal and are based on a reflector kinds of test. The initial calibration is employed until the end of the activity as long as recalibration is not needed. This calibration is very demanding in terms of LED power consumption. Also, when it comes to the PPG signals on human body, it is known that the AC part of the PPG signals matters the most to the algorithms. Additionally, body-specific types of noise make the reflector tests totally different from human body and these differences can be seen in the test results. Accordingly, an improved method is needed for power optimization based on SQMs of the AC component of PPG signals.

A design is typically optimized for AC SNR ($SNR_{AC}$), dictated by the requirements of the system algorithm. The LED current required to meet the $SNR_{AC}$ may be calculated as follows:

$$I_{LED}=S_{DC}/CTR$$

Substituted into the LED equation:

$$I_{LED}=S_{AC}/(CTR \times MI)$$

The above formula can be used to compute what LED current is required to attain the desired SNRAC for a given MI and CTR measured from the user. The AFE noise is set by the configuration of the part and may be measured using a "reflector" setup.

One embodiment is a method for reducing the LED power of a wearable biometric monitoring device without compromising the performance of the VSM algorithms. In accordance with features of one embodiment, a number of statistical and spectral characteristics of raw and filtered PPG signals, referred to as multi-dimensional SQMs, from the measured PPG signals on human tissue are evaluated. The SQMs are subsequently input to a classifying algorithm initially trained to classify the measured PPG signal quality into one of several different quality types or levels. The resulting classification is used to control the LED power in order to conserve power and at the same time maintain the quality of the PPG signal with no detriment to the performance of the VSM algorithms.

Figure 5:
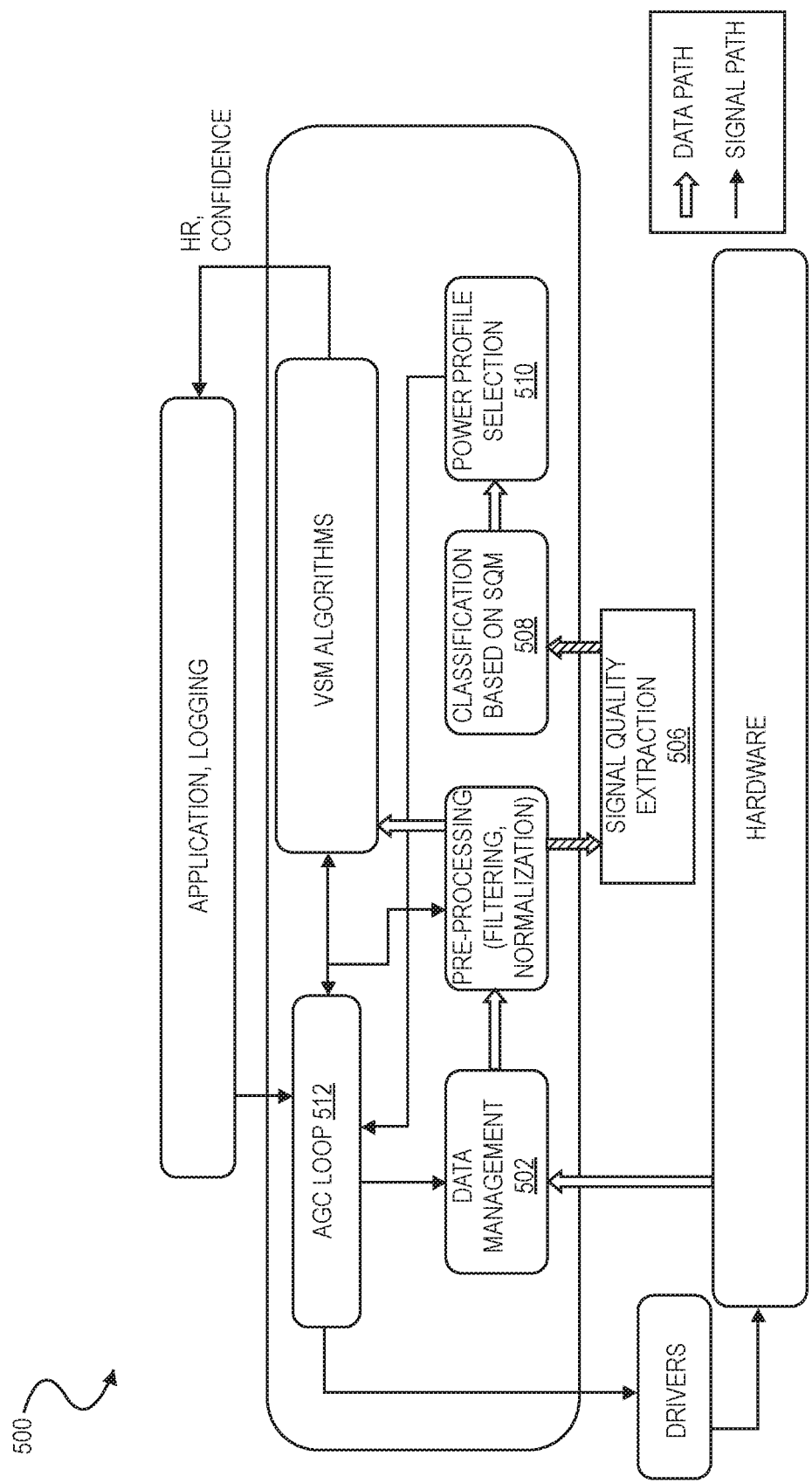
FIG. 5 illustrates a block diagram of software architecture a proposed system for power reduction for wearable monitoring device using SQMs in accordance with embodiments described herein.

FIG. 5 illustrates a high-level block diagram of a power optimization software architecture 500 in accordance with embodiments described herein. In particular, FIG. 5 illustrates the overall system architecture and the related submodules, including a Data Management module 502, a Pre-Processing module 504, a Signal Quality Extraction module 506, a Classification module 508, a Power Profile Selection module 510, an AGC Loop 512, and VSM Algorithms 514.

The Data Management submodule 502 is responsible for providing sensor data to the VSM algorithms 514. Upon data arrival at a FIFO buffer, an interrupt is triggered and timestamps are assigned in an interrupt service routine. Subsequently, the received data, including PPG data, is picked up at scheduled times and placed into a soft buffer, from which it is supplied to blocks of Pre-Processing submodule 504.

The Pre-Processing submodule 504 is responsible for filtering raw PPG signals and removing baseline wandering therefrom. In one embodiment, the filter function of the Pre-Processing submodule 504 has cutoff frequencies at 0.5 Hz (low) and 5 Hz (high) to remove high frequency components of the PPG signal as well as low frequency noise due to changes in capillary density and venous blood volume.

The Signal Quality Extraction submodule 506 is responsible for continuous signal quality assessment after initial calibration. The SQM in accordance with embodiments described herein will be explained in greater detail below.

The Classification submodule 508 classifies the PPG signal quality into one of three levels: Excellent (G1), Acceptable (G2), and Weak (G3). In accordance with features of one embodiment, for training purposes, 1000 recordings of a PPG signal with different parameter sweeps (e.g., LED level, number of pulses, and sampling frequency) were ranked. Signals classified as having Excellent signal quality (G1) included those signals whose shape and morphology was that of typical PPG signals, with special attention paid to the morphology of the PPG signals. Those classified as having Acceptable signal quality (G2) included those signals with good quality for the heart rate information, but whose morphology was not necessarily in keeping with PPG signals. Finally, those classified as having Weak signal quality (G3) included signals that had neither heart rate information in terms of periodicity nor any other useful information related to the PPG signal. Scatter plots of excellent versus acceptable, excellent versus weak, and excellent versus weak and acceptable based on each SQM generated and appropriate thresholds are set based on both visual linear classification and Receiver Operating Characteristic ("ROC") curves. ROC is a measure of performance of each metric in terms of the sensitivity and specificity of the metric to differentiate between true positive, false positive, and false negative outcomes. Using both the ROC curves as well as the scatter plots, a target range may be derived for each SQM, as shown in and described with reference to FIGS. 6A and 6B below.

The Power Profile Selection submodule 510 sets a target signal quality (i.e., G1, G2, or G3) depending on requirements of the particular VSM algorithm and controls (i.e., increases or decreases) LED power to attempt to achieve proximity to the SQM thresholds. In some embodiments, a binary search control scheme is used for performing iterative AGC (doubling or halving the power) in the unsearched power consumption range until sufficient proximity to the SQM target is achieved. Alternatively, fixed step size adjustments may be made on LED current and pulse counts until sufficient proximity to the SQM target is achieved.

Figure 7:
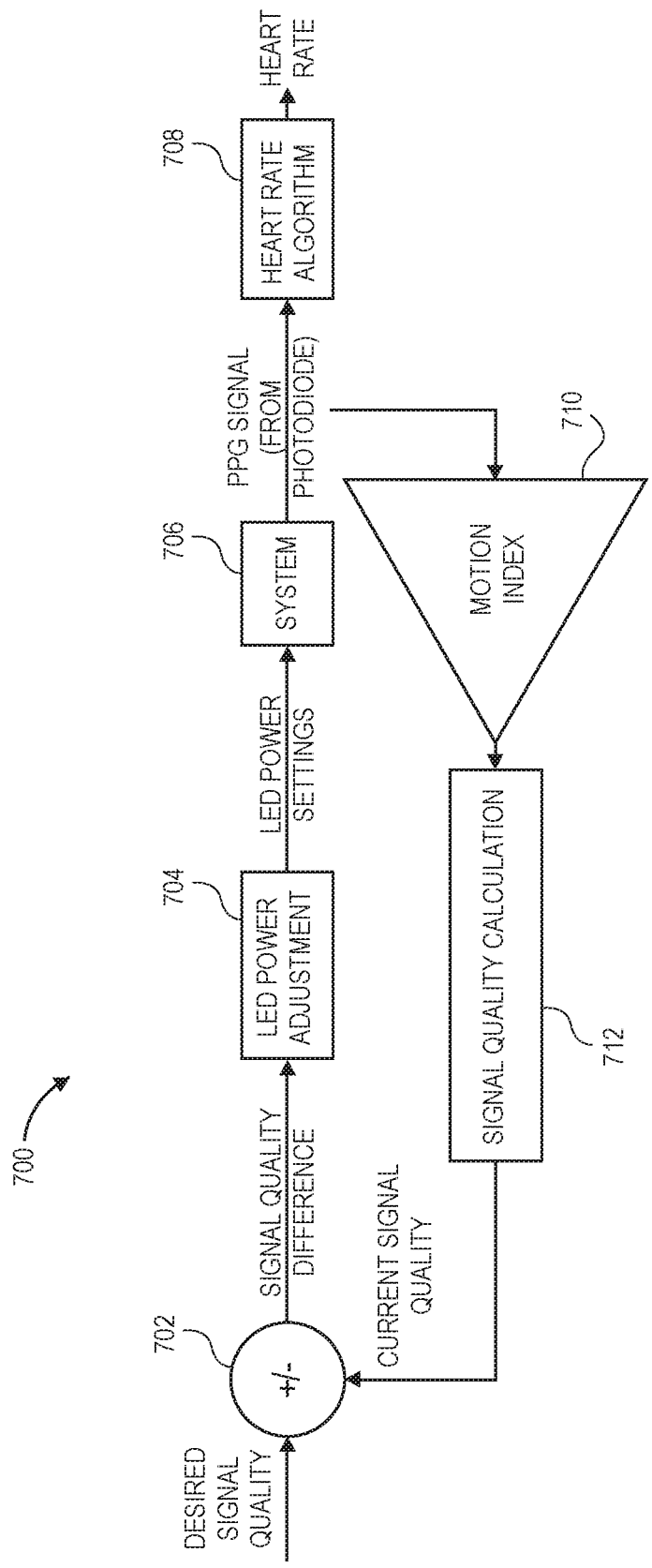
FIG. 7 is a flow diagram illustrating an automatic gain control ("AGC") algorithm for use in a system for power reduction for wearable monitoring device using SQMs in accordance with embodiments described herein.

The AGC Loop submodule 512, a flowchart of one embodiment of which is illustrated in FIG. 7, described in detail below, is responsible for periodically monitoring motion index and SQMs and adjusting the power settings as determined by other submodules in the manner described above. The AGC loop 512 monitors PPG signal quality when there is no option and periodically adjusts the LED power setting to optimize for and target desired signal quality. Changing the LED settings may cause DC changes in the PPG signal. When power changes occur, some of the unprocessed PPG data in FIFO buffer will be dropped, which causes some data loss. Accordingly, the AGC Loop submodule interpolates the data packets such that the change in the DC level is observed seamlessly by the VSM algorithms. The AGC Loop submodule also deals with signal saturation (due to power change) and signal drift resulting from variations of blood perfusion.

The VSM Algorithms 514 includes different VSM algorithms that use PPG signals. For example, a heart rate ("HR") estimation algorithm is illustrated in FIG. 7, but the algorithms are a full stack of algorithms for performing VSM, including Heart Rate Variability ("HRV") and continuous blood pressure estimation, for example.

Various statistical and spectral characteristics of the PPG signals were considered for use as SQMs; however, clarity (or periodicity) and relative power were selected for use herein. Other statistical metrics may include entropy index (EI), which quantifies the measure of uncertainty in the signal, kurtosis, which measures the distribution of the PPG signal around the mean, and skewness, which measures how symmetric the PPG signal is around the DC level.

Clarity or periodicity (hereinafter referred to merely as "clarity") of a signal is a measure of how coherent the signal is to a sinusoidal signal. If a signal contains a more accurate repeating wave form, then it has higher clarity. The autocorrelation function (AC) of a PPG signal $p_j$ at time j can be defined as:

$$r_t(\tau) = \sum_{j=t}^{t+M-1-\tau} p_j p_{j+\tau}, \quad (1)$$

where the window size M decreases with increasing lag $\tau$. This AC function has a tapering effect, when a small number of non-zero terms are used in the calculation at larger $\tau$. Next, the Square Difference Function ("SDF") of the PPG signals may be defined as:

$$d_t(\tau) = \sum_{j=t}^{t+M-1-\tau} (p_j - p_{j+\tau})^2 \quad (2)$$
$$= \sum_{j=t}^{t+M-1-\tau} (p_j^2 - p_{j+\tau}^2 - 2p_j p_{j+\tau}).$$

Then, the SDF can be represented as:

$$d_t(\tau) = s_t(\tau) - 2r_t(\tau),$$
$$\text{with } s_t(\tau) = \sum_{j=t}^{t+M-1-\tau} (p_j^2 + p_{j+\tau}^2).$$

To simplify, the Normalized Square Difference Function (NSDF) is defined as follows:

$$q_t(\tau) = 1 - \frac{s_t(\tau) - 2r_t(\tau)}{s_t(\tau)} = \frac{2r_t(\tau)}{s_t(\tau)}. \quad (3)$$

This function $q_t(\tau)$ is between −1 to 1; 1 means perfect correlation, 0 means no correlation, and −1 means negative correlation. Noting that the normalization function $s_t(\tau)$ is the function of the lag $\tau$, it minimizes the edge effects of decreasing the window size and at the same time limits the range. The first major peak of this NSDF is selected as the clarity metric. This value represents how much the signal is correlated with the fundamental frequency of the PPG signal independent of the amplitude or harmonic of the signal.

Relative Power is defined as the ratio of the power of AC PPG signal after bandpass filtering (0.5-5 Hz) to the power of the raw AC PPG signal. This metric represents how much the PPG signal contains noise in the frequency range that is not useful for VSM algorithms. Therefore, the relative power is a useful metric that correlates well with the accuracy of the VSM algorithms.

Figure 6A:
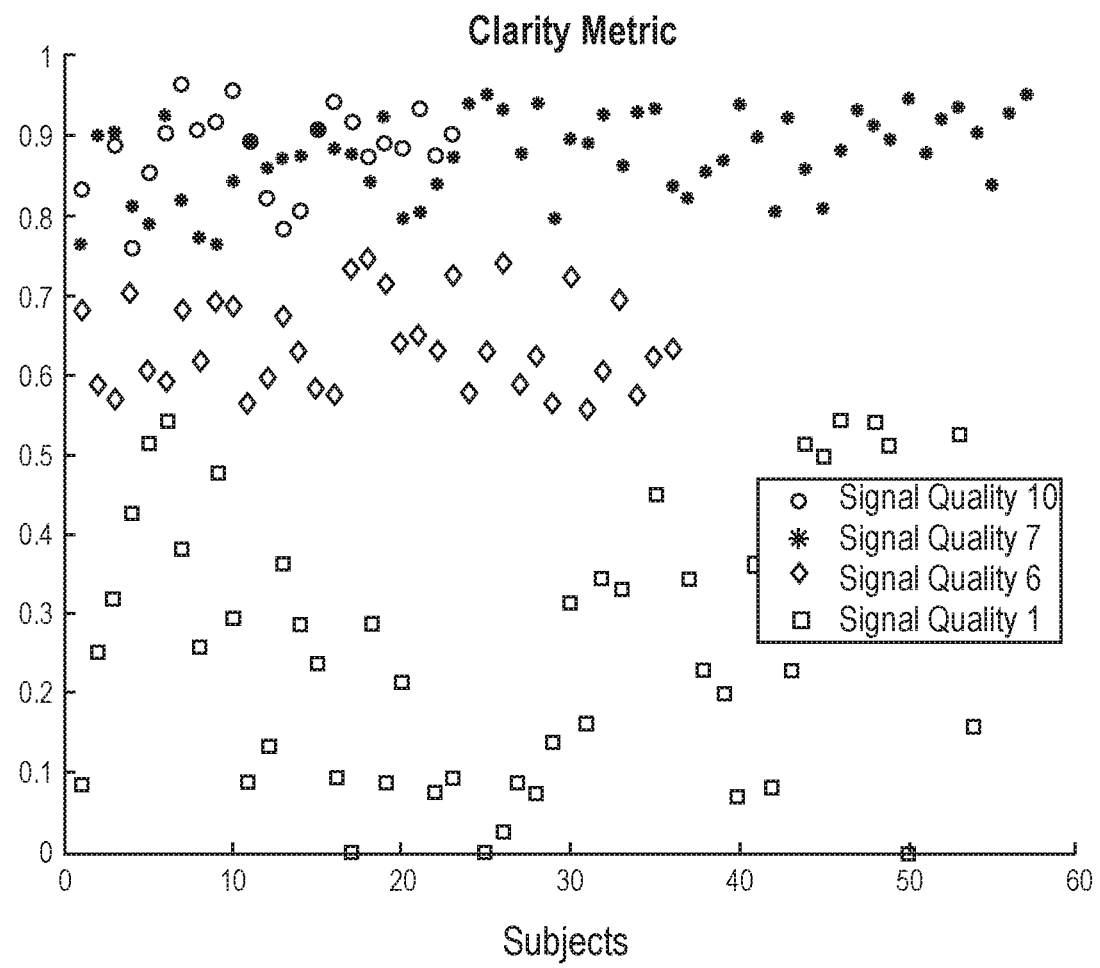
FIG. 6A is a scatter plot of a clarity metric for 1000 recordings of PPG signals on different subjects in accordance with embodiments described herein.
Figure 6B:
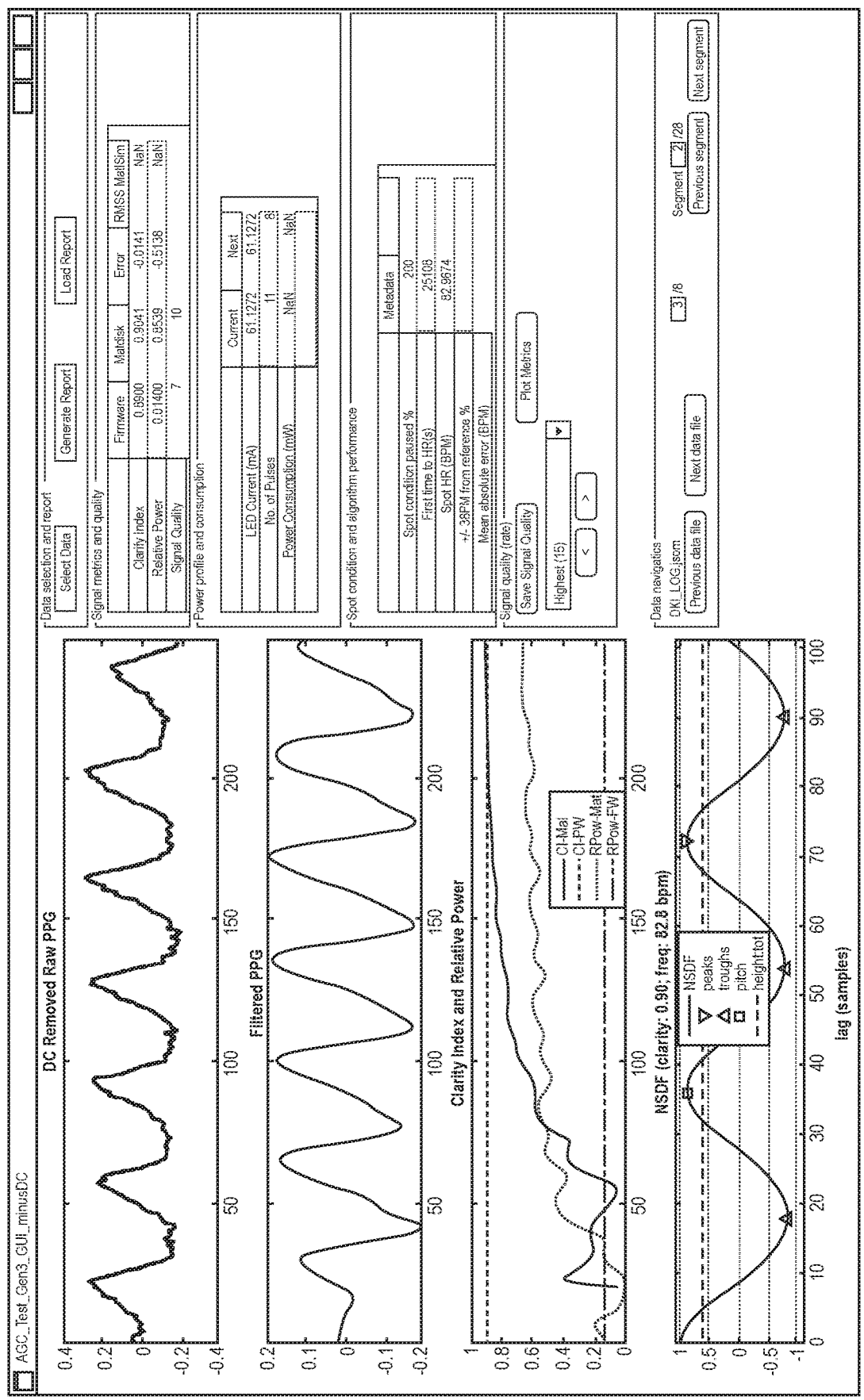
FIG. 6B is an example of a PPG signal with Excellent SQMs in accordance with embodiments described herein.
Figure 6C:
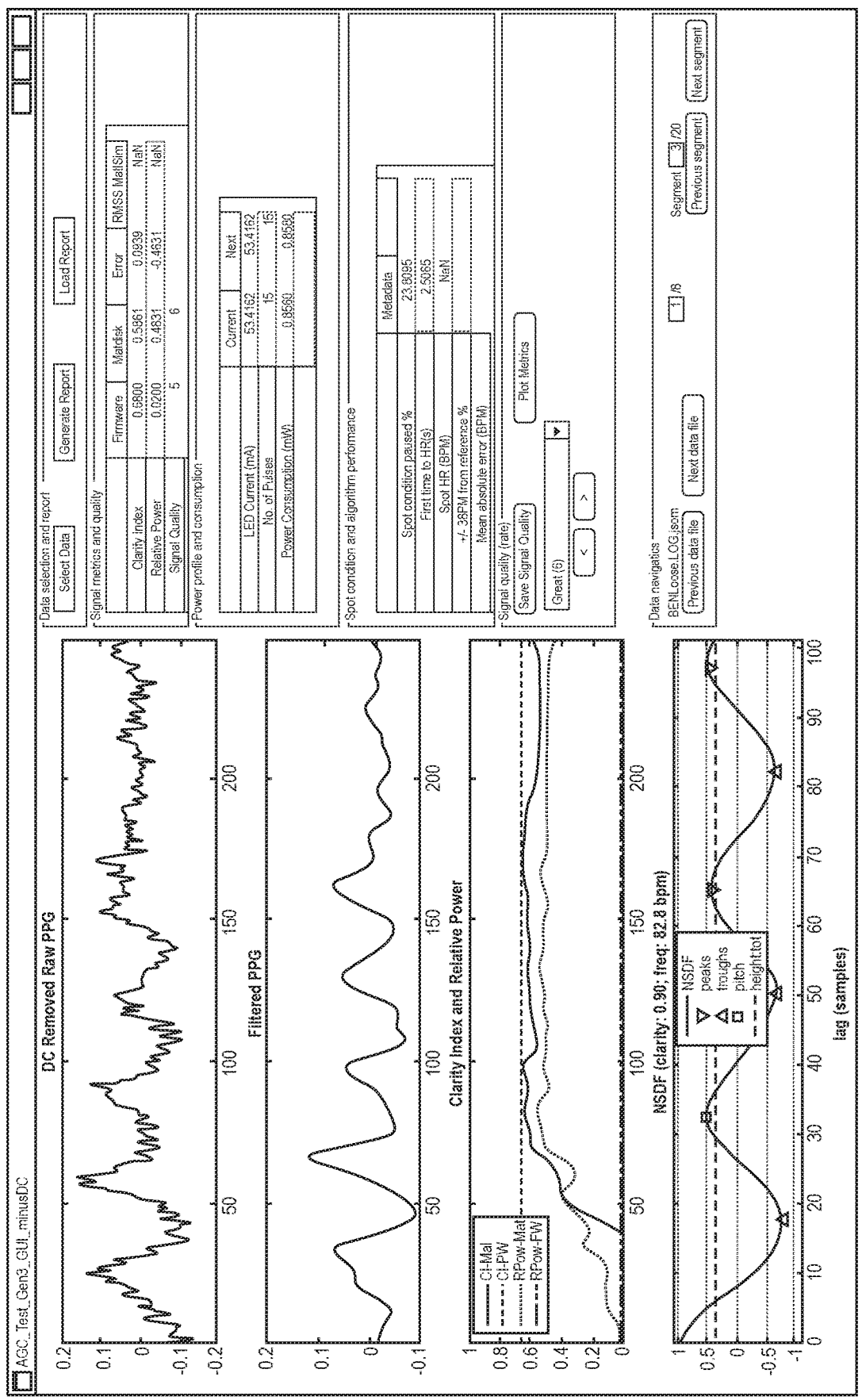
FIG. 6C is an example of a PPG signal with moderate SQMs in accordance with embodiments described herein.
Figure 6D:
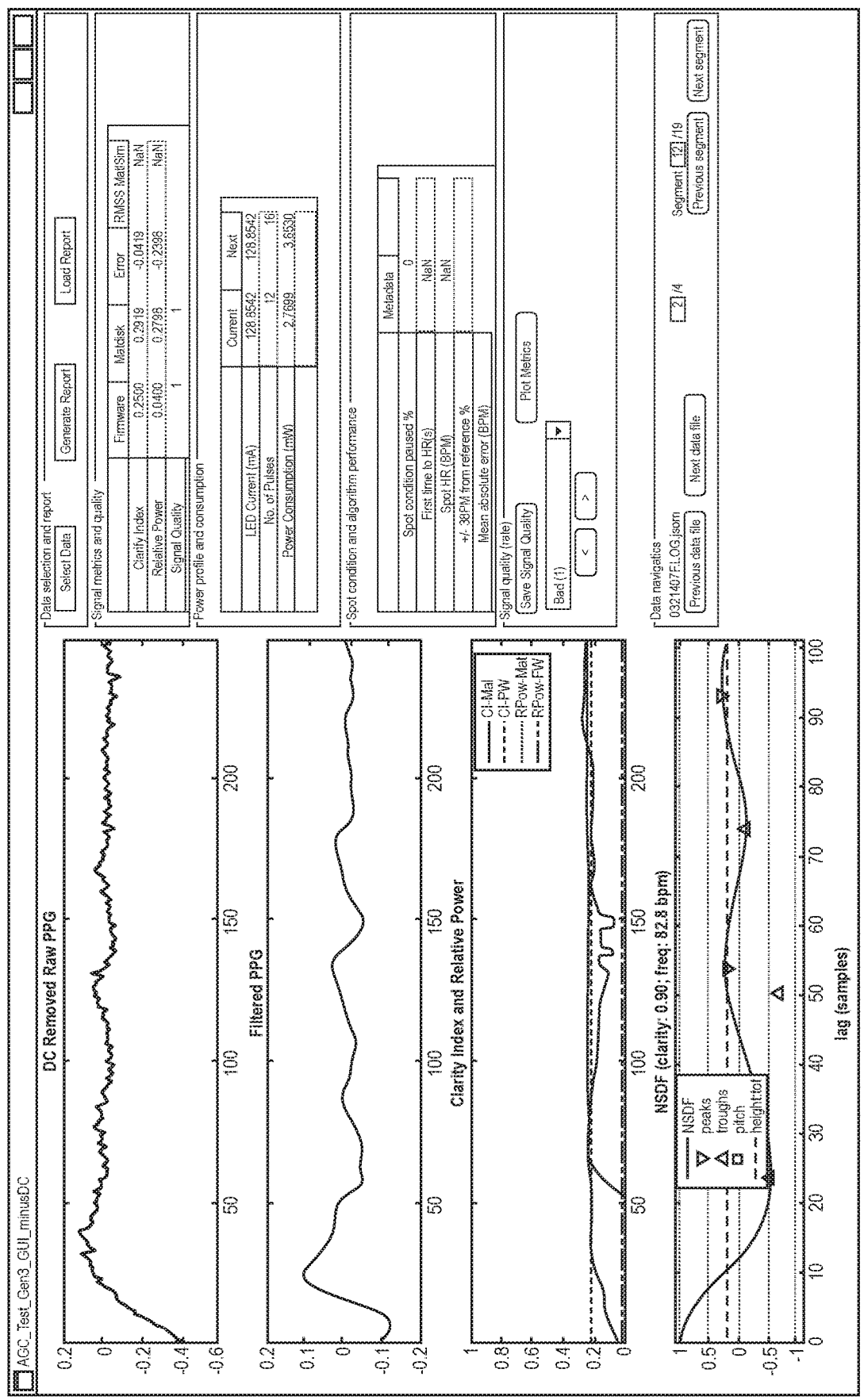
FIG. 6D is an example of a PPG signal with low SQMs in accordance with embodiments described herein.
Figure 8:
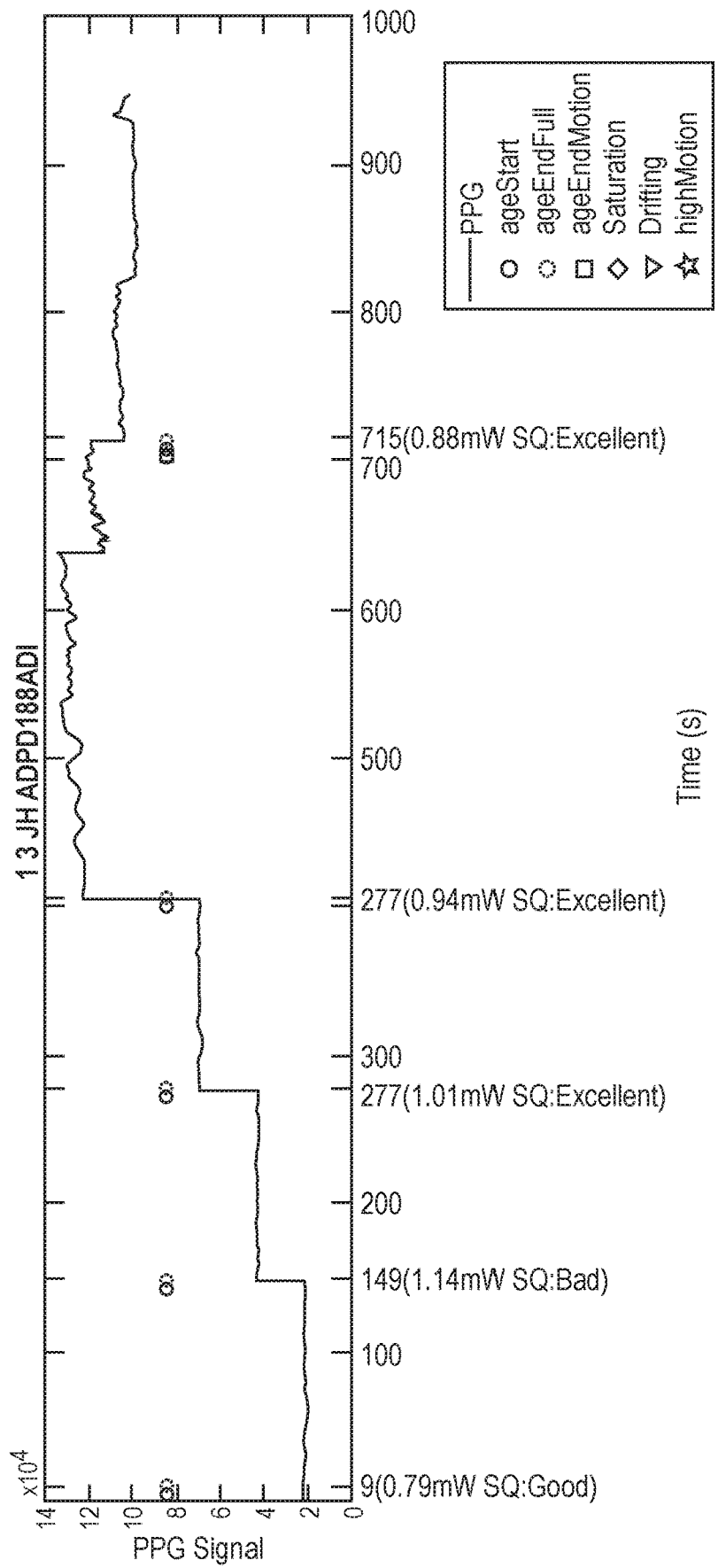
FIG. 8 illustrates the effect of DC changes in the PPG signal due to changes in LED settings because of AGC running continuously.

Results of the embedded power optimization techniques described herein may be described as follows. FIG. 6A illustrates a scatter plot for different subjects with different ratings. Signal quality levels 10 and 7 are "Excellent," signal quality level 6 is "Acceptable," and signal quality 1 is "Weak." The plot in FIG. 6A illustrates that the classification between the three groups is linear. The thresholds for both the dairy and relative power metrics are selected based on the scatter plots. One example of an excellent signal quality is shown in FIG. 6B where the raw PPG signal, the filtered PPG signal and the clarity index and relative power, and the NSDF are shown relative to one another. As previously mentioned, depending on the PPG signal quality, AGC will periodically change the LED settings (i.e., sampling frequency, coarse LED current, fine LED current, and/or the number of pulses) to optimize power. Changing these LED settings will cause DC changes in the PPG signal, as shown in FIG. 8. In particular, FIG. 8 illustrates that for a single subject and during different activities of sitting, walking, and running when the AGC is enabled, the PPG SQM is evaluated and the LED settings are selected to change the signal level. FIG. 6C is an example of a PPG signal with moderate SQMs in accordance with embodiments described herein. FIG. 6D is an example of a PPG signal with low SQMs in accordance with embodiments described herein.

FIG. 7 is a flowchart illustrating a method implemented by an AGC loop 700 for continuously evaluating SQM(s) by obtaining PPG and accelerometer data from the optical sensor and iteratively updating LED settings until a targeted SQM is (or targeted SQMs are) achieved. As shown in FIG. 7, a desired signal quality is compared to a current signal quality at a comparator step 702 to determine a difference in signal quality ("signal quality difference") between the two. It will be noted that this difference may be a positive difference (e.g., the current signal quality is greater than the desired signal quality) or a negative difference (e.g., the current signal quality is less than the desired signal quality). The signal quality difference is used by an LED power adjustment step 704 to adjust the LED power level by adjusting power consumption parameters (e.g., current level and/or pulse rate) of the LED(s) of the system 706. The system 706 (including the optical sensor/LED) continues to output PPG signals to a heart rate algorithm 708. PPG signals are also input to a motion index step 710, which removes motion artifacts from the PPG signal using XL data and provides the indexed PPG signal to a signal quality calculation step 712, which outputs the current signal quality back to the comparator step 702.

Figure 9:
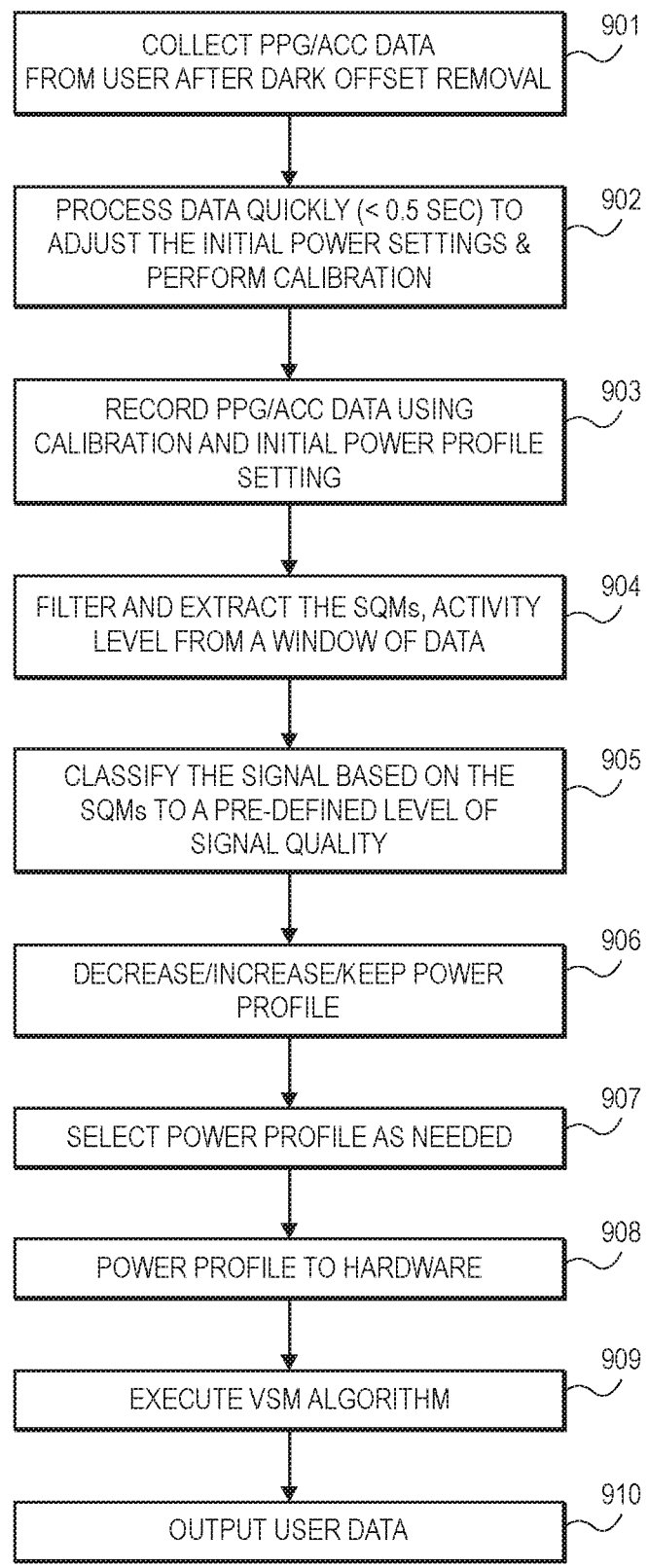
FIGS. 9 and 10 illustrate flow diagrams illustrating example operation of a system for power reduction for a wearable monitoring device using signal quality metrics in accordance with embodiments described herein.

FIG. 9 is a flow diagram illustrating example operation of one embodiment of a system for power reduction for a wearable biometric monitoring device using SQM. In step 901, PPG and ACC data are collected from a subject after dark offset removal. In step 902, the data is processed quickly to adjust and calibrate the initial LED power settings. In step 903, the PPG/ACC data is recorded using the calibration and initial power settings. In step 904, the data is filtered and SQMs and activity level are extracted from a window of the filtered data. In step 905, the signal is classified based on the SQMs to a predefined level of signal quality. In step 906, the power level is decreased (e.g., if the signal quality is Excellent), increased (e.g., if the signal quality is Weak), or maintained (e.g., if the signal quality is Acceptable). In step 907, a power profile is selected and applied to the hardware in step 908. In step 909, the VSM algorithm is run and in step 910, user data is output.

Figure 10:
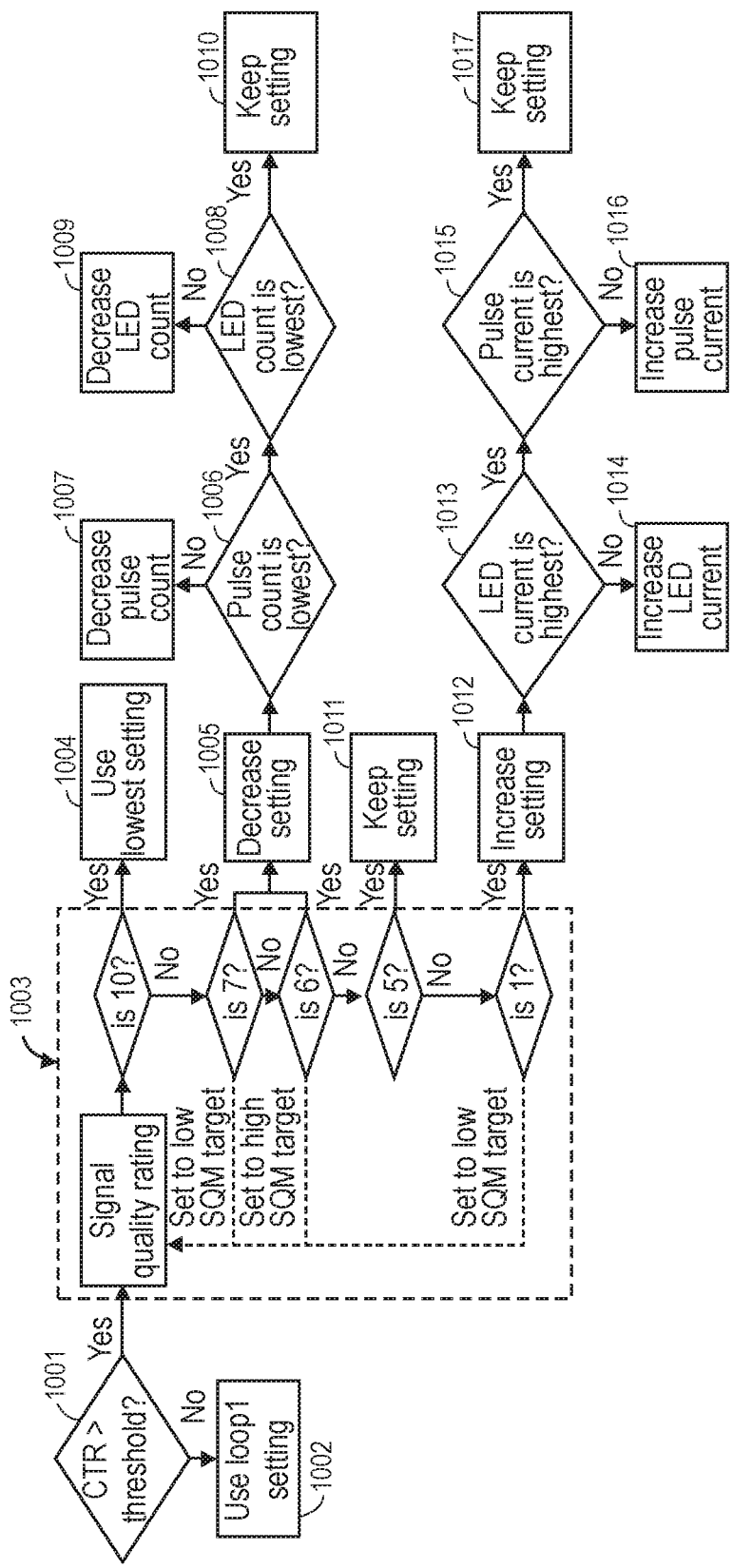

FIG. 10 is a flow diagram illustrating more detail with regard to the classification of the signal and selecting and applying a power profile based on the classification (e.g., steps 905-908 of FIG. 9) in accordance with features of embodiments described herein. As shown in FIG. 10, in step 1001, a determination is made whether the CTR of the system is greater than a preselected threshold value. It will be noted that the preselected threshold value may be application specific. If it is determined in step 1001 that the CTR is not greater than the preselected threshold value, in step 1002, no changes is made to the power profile (i.e., the current settings are maintained). If it is determined in step 1001 that the CTR is greater than the preselected threshold value, execution proceeds to steps 1003, in which the SQM of the signal is rated (e.g., step 905 of FIG. 9). If it is determined that the SQM rating is at the highest possible level (e.g., level 10), in step 1004, the power profile is decreased to the lowest setting (e.g., lowest pulse count and lowest LED current). If it is determined in steps 1003 that the SQM rating is above average (e.g., level 6 or 7), in step 1005, the power profile setting is decreased as follows. In step 1006, a determination is made whether the pulse count is at the lowest setting. If it is determined in step 1006 that the pulse count is not at the lowest setting, execution proceeds to step 1007, in which the pulse count is decreased. If it is determined in step 1006 that the pulse count is at the lowest setting, in step 1008, a determination is made whether the LED current is at the lowest setting. If it is determined in step 1008 that the LED current is not at the lowest setting, in step 1009, the LED current is decreased. If it is determined in step 1008 that the LED current is at the lowest setting, in step 1010, the power profile setting is maintained.

If it is determined in steps 1003 that the SQM rating moderate/acceptable (e.g., level 5), in step 1011, the power profile setting is maintained. If it is determined in steps 1003 that the SQM rating is unacceptably low (e.g., level 1), in step 1012, the power profile setting is increased as follows. In step 1013, a determination is made whether the LED current is at the highest setting. If it is determined in step 1013 that the LED current is not at the highest setting, in step 1014, the LED current is increased. If it is determined in step 1013 that the LED current is at the highest setting, in step 1015, a determination is made whether the pulse count is at the highest setting. If it is determined in step 1015 that the pulse count is not at the highest setting, in step 1016, the pulse count is increased. If it is determined in step 1015 that the pulse count is at the highest setting, in step 1017, the current power profile is maintained.

Example 1 is a method comprising collecting photoplethysmography ("PPG") data associated with a user using a wearable monitoring device; extracting a signal quality metric ("SQM") from the collected PPG data; classifying the PPG data based on the extracted SQM into one of a plurality of signal quality levels; and determining based on the classification whether to increase, decrease, or maintain a power level of an LED of the wearable monitoring device.

In Example 2, the method of Example 1 may further include performing initial processing on the collected PPG data and using the results of the initial processing to calibrate the wearable monitoring device prior to the extracting the SQM.

In Example 3, the method of any of Examples 1 and 2 may further include noise filtering the collected PPG data prior to the extracting the SQM.

In Example 4, the method of any of Examples 1-3 may further include selecting a power profile for the LED based on the classification, wherein the selected power profile indicates at least one of a sampling frequency, a coarse LED current, a fine LED current, and a number of LED pulses.

In Example 5, the method of any of Examples 1-4 may further include applying the selected power profile to the LED.

In Example 6, the method of any of Examples 1-5 may further include executing at least one Vital Signs Monitoring ("VSM") algorithm using the PPG data.

In Example 7, the method of any of Examples 1-6 may further include the SQM comprising at least one of signal clarity and relative power.

In Example 8, the method of any of Examples 1-7 may further include the classifying the PPG data based on the extracted SQM into one of a plurality of signal quality levels comprising classifying the PPG data into a first signal quality level corresponding to excellent signal quality and decreasing a power level of the LED.

In Example 9, the method of any of Examples 1-8 may further include the classifying the PPG data based on the extracted SQM into one of a plurality of signal quality levels comprising classifying the PPG data into a second signal quality level corresponding to acceptable signal quality and maintaining a power level of the LED.

In Example 10, the method of any of Examples 1-9 may further include the classifying the PPG data based on the extracted SQM into one of a plurality of signal quality levels comprising classifying the PPG data into a third signal quality level corresponding to low signal quality and increasing a power level of the LED.

Example 11 is a system comprising an optical sensor for producing photoplethysmography ("PPG") data associated with a user and a processor module configured for extracting a signal quality metric ("SQM") from the collected PPG data; classifying the PPG data based on the extracted SQM into one of a plurality of signal quality levels; and determining based on the classification whether to increase, decrease, or maintain a power level of an LED of the wearable monitoring device.

In Example 12, the system of Example 11 may further include the system being incorporated into a wearable monitoring device.

In Example 13, the system of any of Examples 10-12 may further include the wearable monitoring device being battery powered.

In Example 14, the system of any of Examples 10-13 may further include the optical sensor being in contact with skin of the user.

In Example 15, the system of any of Examples 10-14 may further include the processor module being further configured for selecting a power profile for the LED based on the classification, wherein the selected power profile indicates at least one of a sampling frequency, a coarse LED current, a fine LED current, and a number of LED pulses; and applying the selected power profile to the LED.

In Example 16, the system of any of Examples 10-15 may further include the SQM comprising at least one of signal clarity and relative power.

In Example 17, the system of any of Examples 10-16 may further include the classifying the PPG data based on the extracted SQM into one of a plurality of signal quality levels comprising at least one of classifying the PPG data into a first signal quality level corresponding to excellent signal quality and decreasing a power level of the LED; classifying the PPG data into a second signal quality level corresponding to acceptable signal quality and maintaining a power level of the LED; and classifying the PPG data into a third signal quality level corresponding to low signal quality and increasing a power level of the LED.

Example 18 is a method comprising generating a photoplethysmography ("PPG") signal associated with a user using a wearable monitoring device comprising an optical sensor and a processing module; evaluating a quality of the PPG signal; classifying the PPG signal into one of a plurality of signal quality levels based on the evaluated quality; determining based on the classification whether to increase, decrease, or maintain a power level of an LED of the optical sensor; and adjusting a power level of the LED based on results of the determining.

In Example 19, the method of Example 18 may further include the adjusting further comprising selecting a power profile for the LED based on the classification, wherein the selected power profile indicates at least one of sampling frequency, a coarse LED current, a fine LED current, and a number of LED pulses; and applying the selected power profile to the LED.

In Example 20, the method of any of Examples 18-19 may further include the evaluating a quality of the PPG signal comprising evaluating at least one of signal clarity and relative power.

It should be noted that all of the specifications, dimensions, and relationships outlined herein (e.g., the number of elements, operations, steps, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, exemplary embodiments have been described with reference to particular component arrangements. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system may be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and may accommodate a large number of components, as well as more complicated/sophisticated arrangements and configurations. Accordingly, the examples provided should not limit the scope or inhibit the broad teachings of the electrical circuits as potentially applied to myriad other architectures.

It should also be noted that in this Specification, references to various features (e.g., elements, structures, modules, components, steps, operations, characteristics, etc.) included in "one embodiment", "exemplary embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It should also be noted that the functions related to circuit architectures illustrate only some of the possible circuit architecture functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Note that all optional features of the device and system described above may also be implemented with respect to the method or process described herein and specifics in the examples may be used anywhere in one or more embodiments.

The "means for" in these instances (above) may include (but is not limited to) using any suitable component discussed herein, along with any suitable software, circuitry, hub, computer code, logic, algorithms, hardware, controller, interface, link, bus, communication pathway, etc.

Note that with the example provided above, as well as numerous other examples provided herein, interaction may be described in terms of two, three, or four network elements. However, this has been done for purposes of clarity and example only. In certain cases, it may be easier to describe one or more of the functionalities of a given set of flows by only referencing a limited number of network elements. It should be appreciated that topologies illustrated in and described with reference to the accompanying FIGURES (and their teachings) are readily scalable and may accommodate a large number of components, as well as more complicated/sophisticated arrangements and configurations. Accordingly, the examples provided should not limit the scope or inhibit the broad teachings of the illustrated topologies as potentially applied to myriad other architectures.

It is also important to note that the steps in the preceding flow diagrams illustrate only some of the possible signaling scenarios and patterns that may be executed by, or within, communication systems shown in the FIGURES. Some of these steps may be deleted or removed where appropriate, or these steps may be modified or changed considerably without departing from the scope of the present disclosure. In addition, a number of these operations have been described as being executed concurrently with, or in parallel to, one or more additional operations. However, the timing of these operations may be altered considerably. The preceding operational flows have been offered for purposes of example and discussion. Substantial flexibility is provided by communication systems shown in the FIGURES in that any suitable arrangements, chronologies, configurations, and timing mechanisms may be provided without departing from the teachings of the present disclosure.

Although the present disclosure has been described in detail with reference to particular arrangements and configurations, these example configurations and arrangements may be changed significantly without departing from the scope of the present disclosure. For example, although the present disclosure has been described with reference to particular communication exchanges, embodiments described herein may be applicable to other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 142 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A method comprising:
    collecting photoplethysmography ("PPG") data associated with a user using a wearable monitoring device;
    extracting a signal quality metric ("SQM") from the collected PPG data;
    classifying the PPG data based on the extracted SQM into one of a plurality of signal quality levels;
    setting a target SQM;
    determining based on classification of the PPG data and the target SQM whether to increase, decrease, or maintain a power level of a light emitting diode (LED) of the wearable monitoring device for an optimized power level; and
    outputting user data collected at the optimized power level,
    wherein the SQM comprises signal clarity.

2. The method of claim 1 further comprising:
    performing initial processing on the collected PPG data and using results of the initial processing to calibrate the wearable monitoring device prior to the extracting the SQM.

3. The method of claim 1 further comprising noise filtering the collected PPG data prior to the extracting the SQM.

4. The method of claim 1 further comprising selecting a power profile for the LED based on the classification, wherein the selected power profile indicates at least one of a sampling frequency, a coarse LED current, a fine LED current, and a number of LED pulses.

5. The method of claim 4 further comprising applying the selected power profile to the LED.

6. The method of claim 1 further comprising executing at least one Vital Signs Monitoring ("VSM") algorithm using the PPG data.

7. The method of claim 1, wherein the SQM further comprises relative power.

8. The method of claim 1, wherein the classifying the PPG data based on the extracted SQM into one of the plurality of signal quality levels comprises classifying the PPG data into a first signal quality level corresponding to excellent signal quality, the method further comprising decreasing the power level of the LED.

9. The method of claim 1, wherein the classifying the PPG data based on the extracted SQM into one of the plurality of signal quality levels comprises classifying the PPG data into a second signal quality level corresponding to acceptable signal quality, the method further comprising maintaining the power level of the LED.

10. The method of claim 1, wherein the classifying the PPG data based on the extracted SQM into one of the plurality of signal quality levels comprises classifying the PPG data into a third signal quality level corresponding to low signal quality, the method further comprising increasing the power level of the LED.

11. A system comprising:
    an optical sensor for producing photoplethysmography ("PPG") data associated with a user; and
    a processor configured to:
        extract a signal quality metric ("SQM") from the PPG data;
        classify the PPG data based on the extracted SQM into one of a plurality of signal quality levels;
        set a target SQM;
        determine based on classification of the PPG data and the target SQM whether to increase, decrease, or maintain a power level of a light emitting diode (LED) of a wearable monitoring device for an optimized power level; and
        output user data collected at the optimized power level,
    wherein the SQM comprises signal clarity.

12. The system of claim 11, wherein the system is incorporated into the wearable monitoring device.

13. The system of claim 12, wherein the wearable monitoring device is battery powered.

14. The system of claim 11, wherein the optical sensor is adapted to be in contact with skin of the user.

15. The system of claim 11, wherein the processor is further configured to:
    select a power profile for the LED based on the classification, wherein the selected power profile indicates at least one of a sampling frequency, a coarse LED current, a fine LED current, and a number of LED pulses; and
    apply the selected power profile to the LED.

16. The system of claim 11, wherein the SQM further comprises relative power.

17. The system of claim 11, wherein classify the PPG data based on the extracted SQM into one of the plurality of signal quality levels comprises at least one of:
    classify the PPG data into a first signal quality level corresponding to excellent signal quality and decreasing the power level of the LED;
    classify the PPG data into a second signal quality level corresponding to acceptable signal quality and maintaining the power level of the LED; and
    classify the PPG data into a third signal quality level corresponding to low signal quality and increasing the power level of the LED.

18. A method comprising:
    generating a photoplethysmography ("PPG") signal associated with a user using a wearable monitoring device comprising an optical sensor and a processing module;
    evaluating a quality of the PPG signal, including signal clarity;
    classifying the PPG signal into one of a plurality of signal quality levels based on the evaluated quality;
    setting a target signal quality metric ("SQM"); determining based on classification of the PPG signal and the target SQM whether to increase, decrease, or maintain a power level of a light emitting diode (LED) of the wearable device for an optimized power level;
    adjusting the power level of the LED based on results of the determining; and outputting user data collected at the optimized power level,
    wherein the SQM comprises signal clarity.

19. The method of claim 18, wherein the adjusting further comprises:
    selecting a power profile for the LED based on the classification, wherein the selected power profile indicates at least one of sampling frequency, a coarse LED current, a fine LED current, and a number of LED pulses; and
    applying the selected power profile to the LED.

20. The method of claim 18, wherein evaluating the quality of the PPG signal further comprises evaluating relative power.

* * * * *